United States Patent [19]

Ogawa et al.

[11] Patent Number: 4,950,750
[45] Date of Patent: Aug. 21, 1990

[54] GLYCOLIPID CONTAINING N-GLYCOLYLNEURAMINIC ACID AND METHOD OF PRODUCING THE SAME

[75] Inventors: Tomoya Ogawa, Musashino; Masaaki Numata, Kawagoe; Mamoru Sugimoto, Niiza; Shohei Shibayama, Tokorozawa; Shoji Yoshimura, Iruma; Masayoshi Ito, Kunitachi; Yoshiyasu Shitori, Tokyo, all of Japan

[73] Assignee: Mect Corporation, Tokyo, Japan

[21] Appl. No.: 110,133

[22] Filed: Oct. 19, 1987

[30] Foreign Application Priority Data

Oct. 20, 1986 [JP] Japan .................... 61-248981
Oct. 27, 1986 [JP] Japan .................... 61-254992

[51] Int. Cl.$^5$ .................... C07H 5/00; C07H 1/00; C07H 11/00
[52] U.S. Cl. .................... 536/18.7; 536/53; 536/55.1; 536/55.2; 536/55.3; 536/124; 536/121; 536/17.2
[58] Field of Search .................... 536/18.7, 53, 55.1, 536/55.2, 55.3, 17.2, 124; 514/54; 260/404

[56] References Cited

U.S. PATENT DOCUMENTS

4,774,326 9/1988 Shibayama et al. ................ 536/55.3

FOREIGN PATENT DOCUMENTS

60-190745 9/1985 Japan .
63-035588 2/1988 Japan .................... 536/53

OTHER PUBLICATIONS

Sugimoto et al., Glycoconjugate J (1985) 2:5–9.

*Primary Examiner*—Ronald W. Griffin
*Assistant Examiner*—Everett White
*Attorney, Agent, or Firm*—Jacobs & Jacobs

[57] ABSTRACT

The present invention provides ganglioside-related compounds expressed by the following formula:

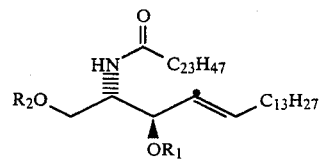

(wherein $R_1$ denotes a hydrogen atom or $SiR_3R_4R_5$ (wherein $R_3$ and $R_4$ each denotes a methyl or phenyl group, and $R_5$ denotes a tertiary butyl or dimethylphenylmethyl group), and $R_2$ denotes a hydrogen atom, a trityl group, or

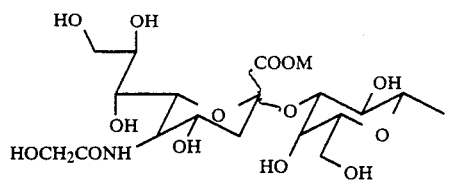

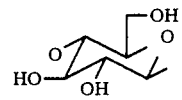

(wherein M denotes an alkali metal atom)) and methods of producing the same. These ganglioside-related compounds are useful as markers for the early detection of cancer and in the immunotherapy for cancer.

19 Claims, No Drawings

GLYCOLIPID CONTAINING N-GLYCOLYLNEURAMINIC ACID AND METHOD OF PRODUCING THE SAME

BACKGROUND OF THE INVENTION (1) Field of the Invention

The present invention relates to ganglioside-related compounds which exhibit Hanganatziu-Deicher antigen activity (referred to as "H—D antigen" hereinafter) and methods of producing the same.

The present invention also relates to ceramide-related compounds which are intermediates for synthesizing the above-described ganglioside-related compounds.

(2) Prior Art

The glycolipids of mammalian cells are the glycosidic linkages between lipid structures called ceramides in which fatty acids are amido-bonded to long-chain amino alcohols called sphingosines and sugars, such as glucose, galactose, N-acetylglucosamine, N-acetylgalactosamine, fucose, and sialic acid, in various combinations, and belong to the category of so-called sphinglycolipids. Of these glycolipids, substances containing sialic acid are specifically called gangliosides.

H—D antigens are antigens which were discovered separately by Hanganatziu and Deicher in patients which had been injected with horse antiserums, for the purpose of curing their diseases, during the 1920s, and are known as antigens which react with the infected serums injected, as well as the red blood corpuscles of various animals such as sheep, horses, pigs, rabbits, and guinea pigs. H—D antigens have also recently been extracted as gangliosides from the red blood corpuscles of horses and have been purified to form simple molecules. In addition, it has been proven that gangliosides exhibiting H—D antigen activity are principal glycolipid components of the red blood corpuscles of horses which have been called "hematosides".

It is assumed that the chemical structure of H—D antigens is Gd Neu(2-3) Gal(1-4) Glc-Cer.

Furthermore, at present, H—D antigens have often been detected in the serum of diseased patients, regardless of whether heterologous antiserums have been administered. It has also been recognized that these antigens appear on the surfaces of cancerous lymphocyte cells of humans or domestic fowl.

Since it seems likely that H—D antigens could be used as markers, not only in the early detection of cancer, but also in immunotherapy for cancer, it is expected that they will be applied to the field of the prevention and treatment of cancer.

Most of such ganglioside-related compounds generally reside in the outer molecular layer of the two molecular layers of a cell membrane, and it is considered from the results of recent research that they play important roles in the discrimination and the acceptance and response of information in cells, in a receptor function, in differentiation, and in the proliferation, malignant change, and behavior of cells.

However, it is very difficult to isolate and purify oligosaccharide chains containing sialic acid from living bodies. It has therefore become necessary and indispensable, in order to elucidate the correlation between the accurate biological information on these oligosaccharide chains containing sialic acid and the molecular structures thereof, that these chains should be accurately synthesized.

The inventors have previously developed a method of synthesizing such a ceramide portion of a glycolipid in a stereoselective manner with a good yield (Japanese Patent Laid-Open No. 190745/1985).

When subjected to glycosylation with a sugar chain portion, the above-described ceramide (I) has conventionally been changed into a benzoylated compound (IV) by the method described below:

The compound (I) is treated with trityl chloride in pyridine to produce a tritylated compound (II) which is then treated with benzoyl chloride and dimethylaminopyridine to obtain a trityl-benzoylated compound (III). This compound is treated with para-toluenesulfonic acid to separate a trityl group and produce the benzoylated compound (IV) of the ceramide. In this series of reactions, the benzoylation can be performed without isolating the compounds (II) and (III) ((I)--(IV)).

However, the glycosylation using the above-described benzoylated compound (IV) has the disadvantages described below:

The benzoylated compound (IV) exhibits poor solubility in solvents, such as methylene chloride, benzene, or nitromethane, which are generally used for glycosylation, and thus the glycosylation can be performed only at a low concentration, and the yield of the product obtained from the glycosylation is insufficient (about 30 to 35%).

SUMMARY OF THE INVENTION

The inventors have conducted intensive investigations with a view to solving the above-described problems. As a result, they unexpectedly discovered that the replacement of the benzoyl group in the above-described compound (IV) by various types of silyl moieties produced remarkable effects such as an increase in the solubility of the compound (IV) in solvents, even under the conditions of the above-described glycosylation, and thus they have determined that the reaction could, for example, be performed at a high concentration (of more than about 50%), as well as provide a large increase in the yield of the product. These findings led to the achievement of the present invention.

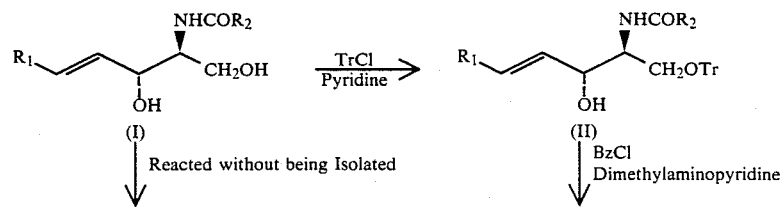

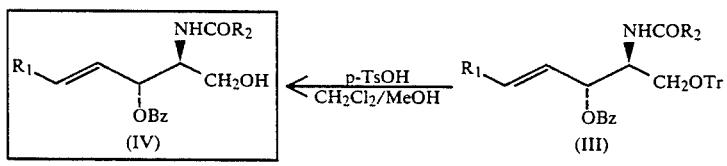

$R_1$: $C_{13}H_{27}$, $R_2$: $C_{23}H_{47}$,
Tr: Trityl Group
Bz: Benzoyl Group It is an object of the present invention to provide novel intermediate ganglioside-related compounds which concern the above-described various medical fields, and a method of producing the same.

It is another object of the present invention to provide novel ceramide-related compounds which are intermediates for the synthesis of the above-described ganglioside-related compounds.

The present invention relates to ganglioside-related compounds of the following formula:

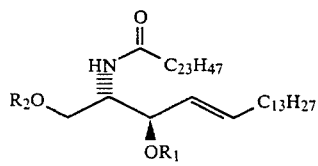

(wherein $R_1$ denotes a hydrogen atom or $SiR_3R_4R_5$ (wherein $R_3$ and $R_4$ each denote a methyl or phenyl group, and $R_5$ denotes a tertiary butyl or dimethylphenylmethyl group), and $R_2$ denotes a hydrogen atom, trityl group (Tr), or

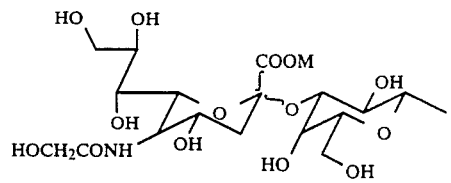

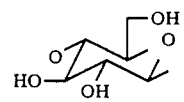

(wherein M denotes an alkali metal atom).

The present invention also relates to a method of producing ganglioside-related compounds characterized by hydrolyzing compounds of the following formula:

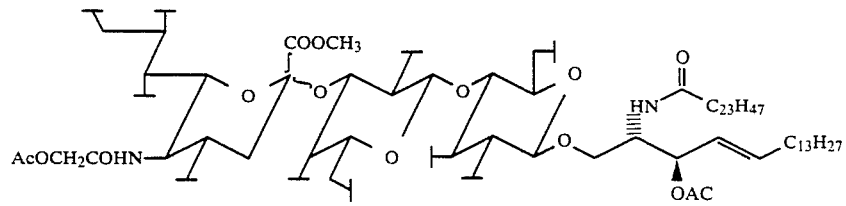

(wherein $\tau$ =OCOCH$_3$ and Ac=COCH$_3$) to produce compounds of the following formula:

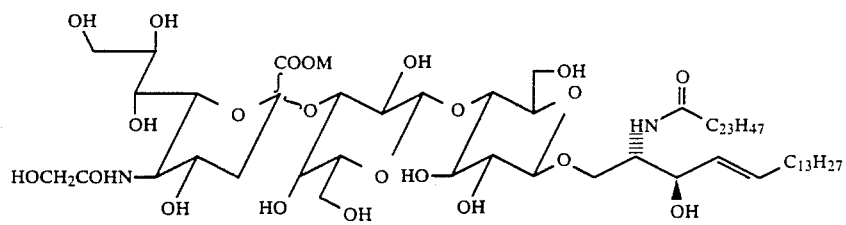

(wherein M denotes an alkali metal atom).

The present invention further relates to a method of producing galglioside-related compounds characterized by acetylating compounds of the following formula:

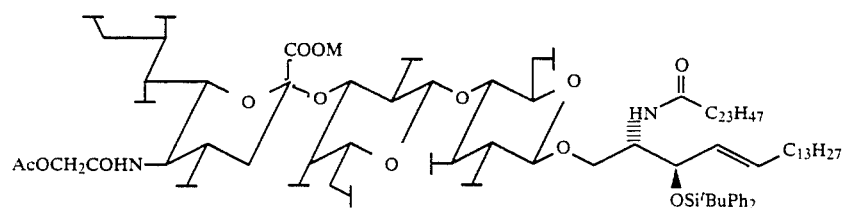

(wherein Si$^t$BuPh$_2$ denotes a diphenyl-t-butylsilyl group) to obtain compounds of the following formula:
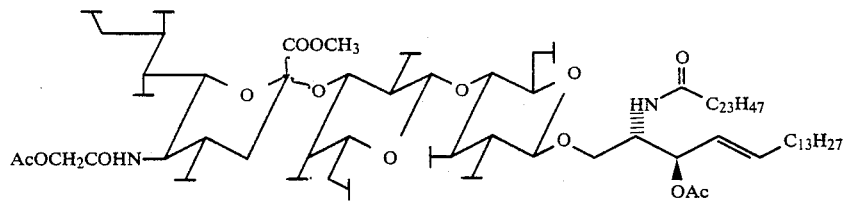
which are then hydrolyzed to obtain compounds of the following formula:
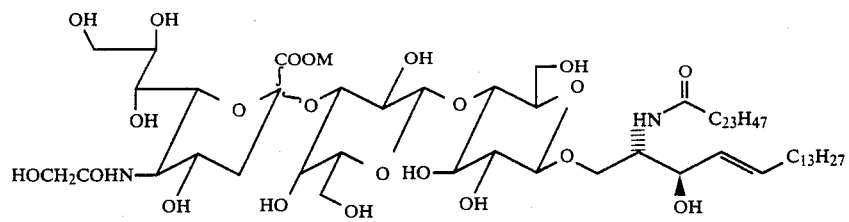
Scheme I
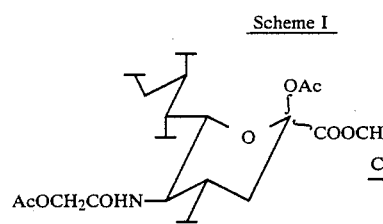
Compound (1)
-continued
Scheme I
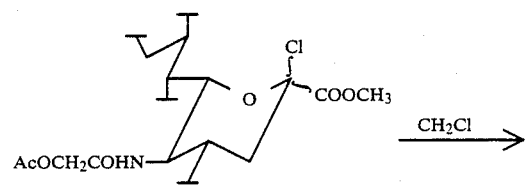
Compound (2)
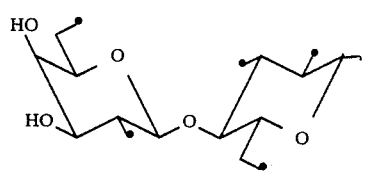
Compound (B)
Scheme II
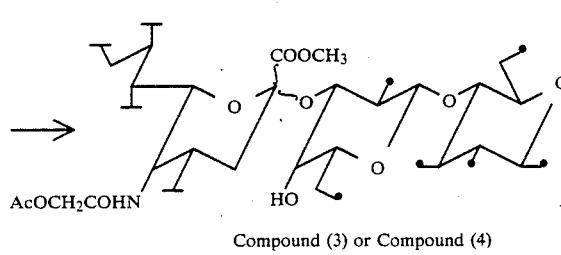
Compound (3) or Compound (4)
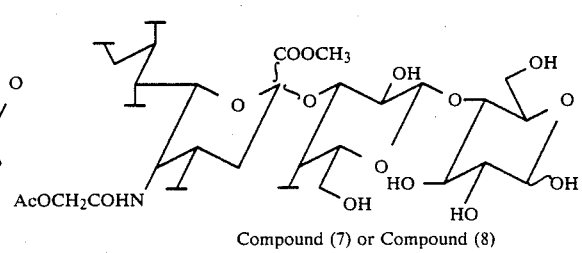
Compound (7) or Compound (8)

Scheme II
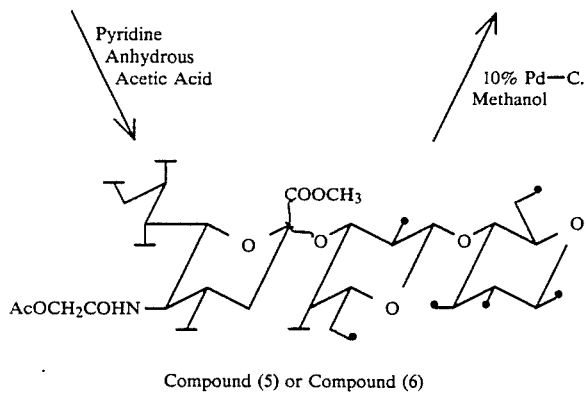
Compound (5) or Compound (6)
Scheme III
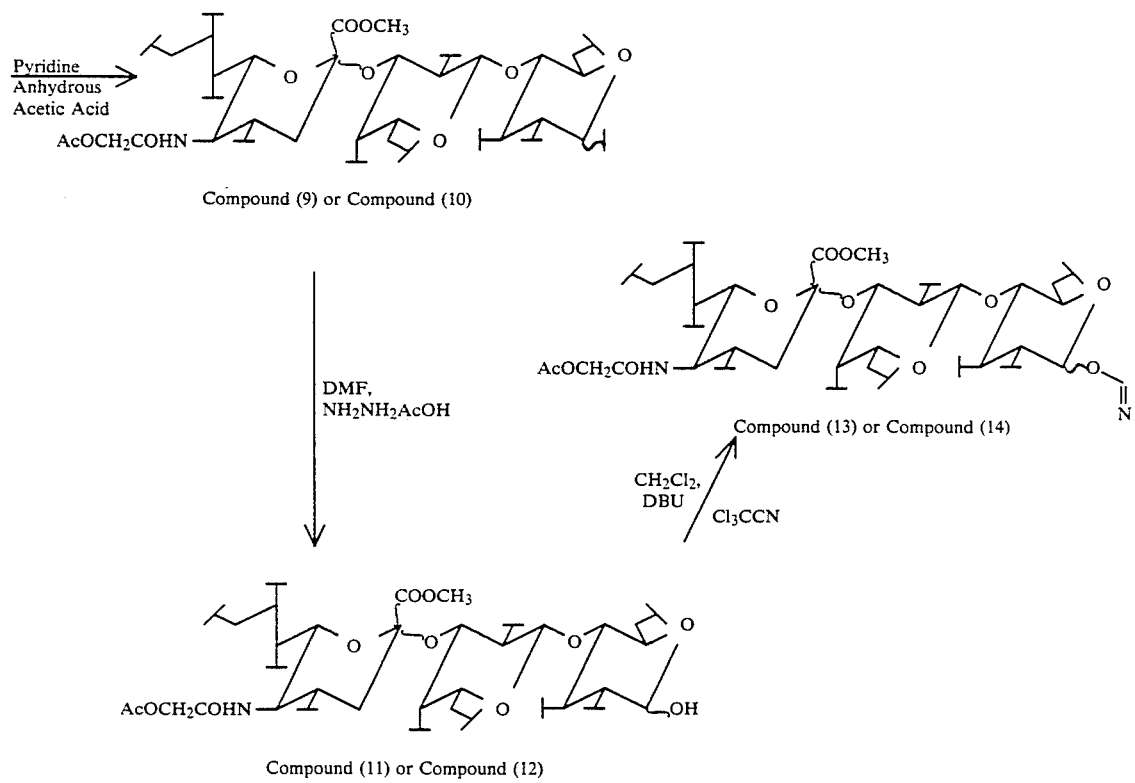
Compound (9) or Compound (10)
Compound (13) or Compound (14)
Compound (11) or Compound (12)
Scheme IV
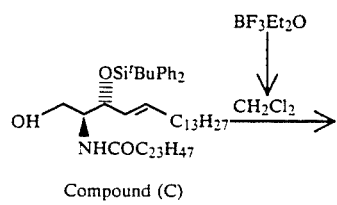
Compound (C)

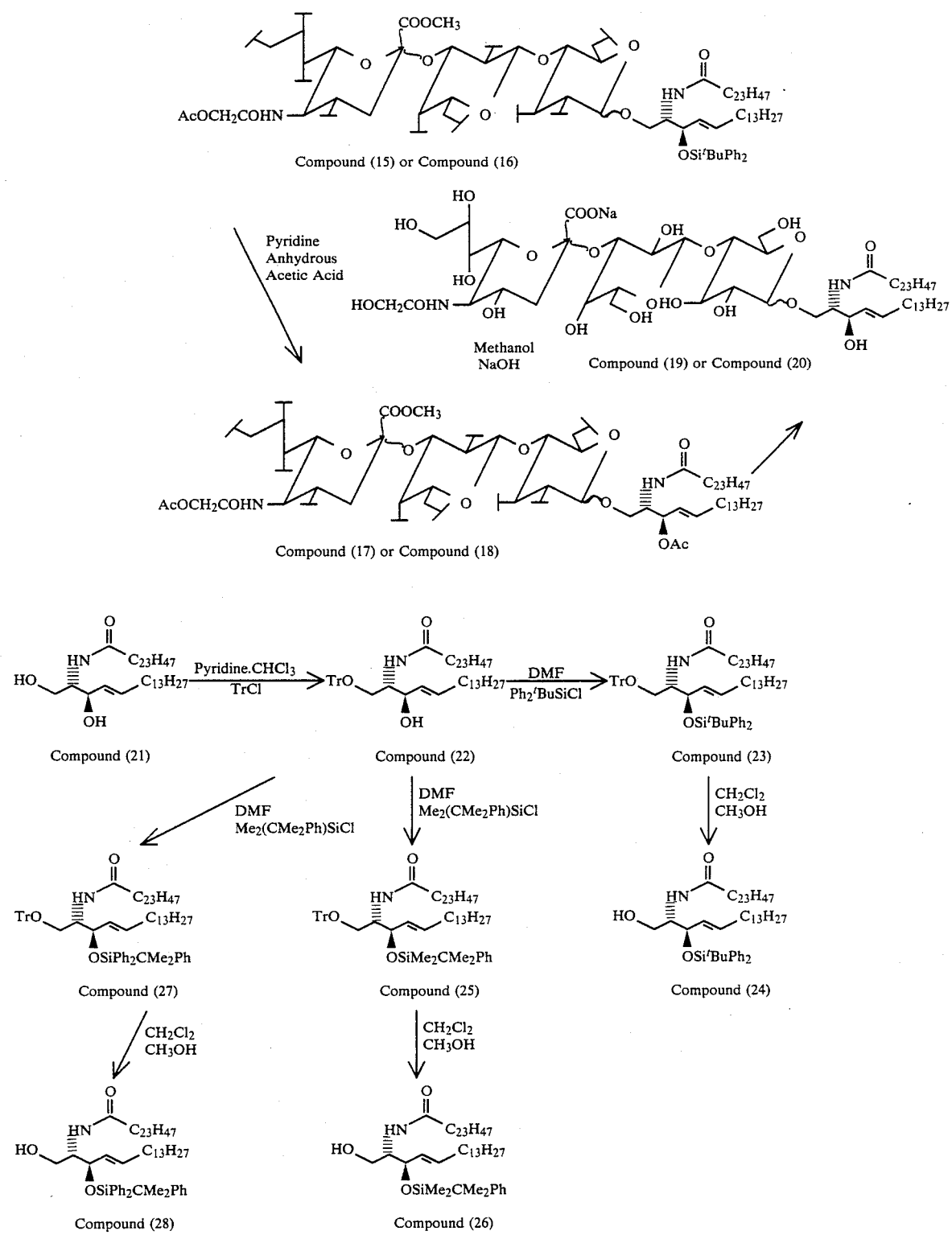
-continued
Scheme IV
DESCRIPTION OF THE PREFERRED EMBODIMENTS
The present invention is described in detail below with reference to Production Schemes I to V, wherein, in the chemical formulae, denotes OCOCH₃ and denotes OCH₂C₆H₅.
(1) Production of Compound (1)
Compound (1) is produced in accordance with the following method:

Formula

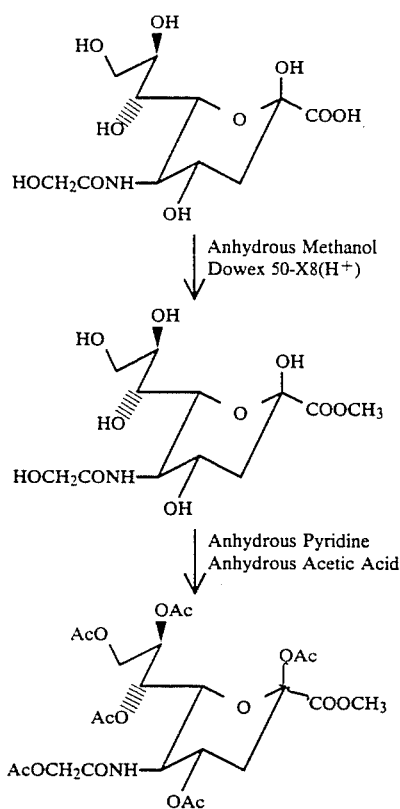

The known compound (A) is prepared by the method described in Monatsh Chem. 97, 654 (1966) (refer to Reference Examples 1 and 2).

(2) Production of Compound (2)

The above-described compound (1) is first added to a solvent such as acetyl chloride, and hydrogen chloride gas is added to the solvent while it is cooled with ice. After being agitated for 24 hours, the thus-obtained solution is concentrated under reduced pressure, and a solvent such as toluene is added to the residue. The obtained solution is subjected to azeotropic distillation to produce compound (2).

(3) Production of Compounds (3) and (4)

Compounds (3) and (4) are produced by reacting the above-described compound (2) with a compound (B) under the reaction conditions described below.

Examples of catalysts, include $HgBr_2$, $Hg(CN)_2$, $AgClO_4$, $AgCO_3$, AgOTf (wherein Tf denotes triflic acid: abbreviated the same way hereinafter), and silver silicate. AgOTf or a mixture of $HgBr_2$ and $Hg(CN)_2$ in a ratio of between 1:3 and 1:1 is preferably used as the catalyst. In addition, $CH_2Cl_2$, benzene, toluene, chloroform, $CH_3CN$, $CH_3NO_2$, or tetrahydrofuran can be used as a solvent. It is preferable to use $CH_2Cl_2$ or tetrahydrofuran as the solvent.

The reaction can be performed at a temperature of within the range of about $-25°$ C. to about $90°$ C. under ice cooling, but preferably at room temperature.

The reaction is performed under agitation for about 30 minutes to about 24 hours. It is preferable to have an agitated reaction of about 24 hours.

The thus-obtained reaction product is purified by a conventional method such as column chromatography.

(4) Production of Compounds (5) and (6)

Compounds (5) and (6) are obtained by acetylating the above-described compounds (3) and (4), respectively, under the reaction conditions given below.

$CH_3COCl$ or $Ac_2O$ can be used as a reagent of this reaction, but $Ac_2O$ is preferable.

Pyridine, TEA, dichloromethane, dichloroethane, or THF can be used as a solvent, and a catalytic amount of dimethylaminopyridine dissolved in pyridine is preferably added to the reaction solution.

The reaction temperature is within the range of about $0°$ C. to about $100°$ C., but is preferably about $60°$ C.

The reaction can be performed under agitation for about 30 minutes to 24 hours, preferably under agitation for 24 hours.

(5) Production of Compounds (7) and (8)

Compounds (7) and (8) are obtained by reacting the above-described compounds (5) and (6), respectively, under the reaction conditions given below.

Pd—C, $Pd(OH)_2$, or $PtO_2$ can be used as a catalyst for the reaction in an atmosphere of hydrogen. A reductant such as HCOOH-MeOH can be also used as a catalyst, but 10% Pd—C is preferable.

Methanol, a mixed solvent of methanol and water, a mixed solvent of methanol and AcOH, or AcOH can be used as a solvent, but methanol is preferable.

The reaction temperature is within the range of ice-cooling temperature to about $60°$ C., but is preferably room temperature.

The reaction time is within the range of about 1 hour to about 24 hours, but is preferably about 24 hours. The reaction is preferably performed under agitation.

The thus-obtained reaction product is purified by filtration.

(6) Production of Compounds (9) and (10)

Compounds (9) and (10) are obtained by acetylating the above-described compounds (7) and (8), respectively, under the reaction conditions given below.

$Ac_2O$ or $CH_3COCl$ can be used as a reagent for the reaction, but $Ac_2O$ is preferable.

Pyridine, TEA, dichloromethane, dichloroethane, DMF, or THF can be used as a solvent, but a catalytic amount of dimethylaminopyridine dissolved in pyridine is preferably added to the reaction solution.

The reaction temperature is within the range of about $0°$ C. to about $80°$ C., but is preferably about $60°$ C.

The reaction time is within the range of about 30 minutes to about 24 hours, but is preferably about 24 hours. It is preferable to agitate the reaction solution.

The thus-obtained reaction product is purified by a conventional method such as column chromatography.

(7) Production of Compounds (11) and (12)

Compounds (11) and (12) are obtained by deacetylating the above-described compounds (9) and (10), respectively, under the reaction conditions given below.

$NH_2NH_2AcOH$ can be used as a reagent for the reaction.

DNF can be used as a solvent.

The reaction temperature is within the range of room temperature to about $80°$ C., but is preferably about $60°$ C.

The reaction time is within the range of about 5 minutes to about 1 hour, preferably about 20 minutes. It is preferable to agitate the reaction solution.

The thus-obtained reaction product is purified by a conventional method such as column chromatography.

(8) Production of Compounds (13) and (14)

Compounds (13) and (14) are obtained by reacting the above-described compounds (11) and (12), respectively, with $Cl_3CCN$ under the reaction conditions given below.

$CCl_3CN$—DBU, $CCl_3CN$—NaH, $CCl_3CN$—$K_2CO_3$, or $CCl_3CN$—BuLi can be used as a catalyst for the reaction, but $CCl_3CN$—DBU is preferable.

Dichloroethane, benzene, toluene, dichloromethane, or chloroform can be used as a solvent, but dichloromethane is preferable.

The reaction temperature is within the range of about $-25°$ C. to about $50°$ C., but is preferably about $0°$ C.

The reaction time is within the range of about 30 minutes to about 12 hours, but is preferably about 4 hours. It is preferable to agitate the reaction solution.

The thus-obtained reaction product is purified by a conventional method such as column chromatography.

(9) Production of Compounds (15) and (16)

Compounds (15) and (16) are obtained by reacting the above-described compounds (13) and (14), respectively, with a compound (C) under the reaction conditions given below.

$BF_3Et_2O$, TMS triflate, $TiCl_4$, $AlCl_3$, or $SnCl_4$ can be used as a catalyst for the reaction, but $BF_3Et_2O$ is preferable.

$CH_2Cl_2$, $C_2H_4Cl_2$, THF, benzene, toluene, $CH_3CN$, $CH_2NO_2$, or ether can be used as a solvent, but $CH_2Cl_2$ is preferable.

The reaction temperature is within the range of about $-25°$ C. to about $60°$ C., but is preferably a temperature under cooling with ice and methanol.

The reaction time is within the range of about 1 hour to about 24 hours, but is preferably about 24 hours. It is preferable to agitate the reaction solution.

(10) Production of Compounds (17) and (18)

Compounds (17) and (18) are obtained by reacting the above-described compounds (15) and (16), respectively, under the reaction conditions given below.

$Bu_4NF$ or HF can be used as a catalyst for the reaction, but $Bu_4NF$ is preferably used.

THF, $CH_3CN$, $CH_3NO_2$, EtOAc, $CH_2Cl_2$, $CHCl_3$, DMF, ether, benzene, or toluene can be used as a solvent, but THF is preferable.

The reaction temperature is within the range of about $0°$ C. to about $50°$ C., but is preferably room temperature.

The reaction time is within the range of about 30 minutes to about 48 hours, and reaction is preferably performed under agitation for about 48 hours.

Then, the following reaction is carried out under the reaction conditions given below.

$Ac_2O$ or $CH_3COCl$ can be used as a reagent for the reaction, but $Ac_2O$ is preferable.

Pyridine, TEA, or dimethylaminopyridine can be used as a solvent, but a catalytic amount of dimethylaminopyridine dissolved in pyridine is preferably added to the reaction solution.

The reaction temperature is within the range of about $0°$ C. to about $80°$ C., but is preferably about $60°$ C.

The reaction time is within the range of about 30 minutes to about 24 hours, but the reaction is preferably performed under agitation for about 6 hours.

The thus-obtained reaction product is purified by a conventional method such as column chromatography.

(11) Production of Compounds (19) and (20)

Compounds (19) and (20) are obtained by deacetylating the above-described compounds (17) and (18), respectively, under the reaction conditions given below.

NaH-MeOH, $K_2CO_3$-MeOH, TEA-MeOH, KOH-MeOH, or NaOH-MeOH can be used as a catalyst for the reaction, but $NaOCH_3$ is preferable and 0.1N $NaOCH_3$ is more preferable.

Methanol, ethanol, propanol, THF, or dioxane can be used as a solvent, but methanol is preferable.

The reaction temperature is within the range of about $-10°$ C. to about $50°$ C., but is preferably room temperature.

The reaction time is within the range of about 30 minutes to about 24 hours, but the reaction is preferably performed under agitation for about 6 hours.

Then, the following reaction is carried out under the reaction conditions given below.

NaOH, KOH, or LiOH can be used as a catalyst for the reaction, but NaOH is preferable.

MeOH—THF, MeOH—dioxane, ethanol—THF, ethanol-dioxane, propanol-dioxane, or propanol-THF can be used as a solvent, and MeOH-THF is preferable.

The reaction temperature is within the range of about $0°$ C. to about $50°$ C., but is preferably room temperature.

The reaction time is within the range of about 30 minutes to about 24 hours, but is preferably about 24 hours. It is preferable to agitate the reaction solution.

The starting raw material for the ceramide-related compounds which are intermediates of the ganglioside-related compounds of the present invention is the above-described compound (22). The ceramide-related compounds can be obtained in accordance with the steps described below.

(1) Production of Compound (1) of the Following Formula:

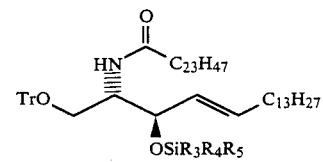

(wherein $R_3$, $R_4$ and $R_5$ each denotes the same as that described above)

Compounds (23), (25), and (27) are obtained from compound (22) under the reaction conditions given below.

$Ph_2^tBuSiCl$, $Ph_2(CMe_2Ph)SiCl$, or $Me_2(CMePh)SiCl$ can be used as a reagent used for each reaction. It is preferable that each reaction is performed in the presence of a chlorine such as imidazole.

Dimethylformamide (DMF), tetrahydrofuran (THF), chloroform, pyridine, or collidine can be used as a solvent, but DMF is preferable.

The reaction temperature is within the range of about $0°$ C. to about $100°$ C., but is preferably within the range of room temperature to $40°$ C.

The reaction time is within the range of about 1 hour to 2 nights, and but is preferably 1 to 2 nights. It is preferable to agitate the reaction solution.

The thus-obtained reaction product is purified by a conventional method such as column chromatography.

(2) Production of Compounds (24), (26), and (28) of the Following Formula:

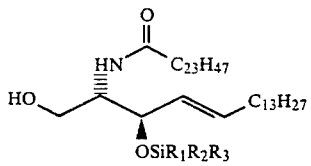

(wherein $R_1$, $R_2$, and $R_3$ each denotes the same as that described above)

Toluenesulfonic acid (abbreviated to TsOH hereinafter), $CF_3COOH$, $CH_3COOH$ (abbreviated to AcOH hereinafter), HCOOH, HCl can be used as a catalyst used in each reaction, but TsOH is preferable.

MeOH-$CH_2Cl_2$, MeOH—$C_2H_4Cl_2$, $CHCl_3$—MeOH, AcOH-MeOH, THF-MeOH, dioxane-MeOH, an aqueous AcOH solution, an aqueous THF solution, or an aqueous dioxane solution can be used as a solvent, but MeOH—$CH_2Cl_2$ is preferable.

The reaction temperature is within the range of about 0° C. to about 80° C., but is preferably room temperature.

The reaction time is within the range of about 30 minutes to one night, but is preferably 1 to 6 hours. It is preferable to agitate the reaction solution.

The thus-obtained reaction product is purified by a conventional method such as column chromatography.

(Availability of the Invention)

The ganglioside-related compounds are useful as markers for the early detection of cancer and in the immunotherapy for cancer.

In addition, the ceramide-related compounds are advantageously used for synthesizing ceramide portions when glycolipids and the above-described ganglioside-related compounds, which are useful as tumor markers, are synthesized.

The present invention is described in detail below with reference to Reference Examples and Examples.

Reference Example 1 (Production of Compound (A') from Compound (A))

Production of methyl
5-N-glycolyl-3,5-dideoxy-β-D-glycero-D-galacto-2-nonulopyranosonate 75 ml of anhydrous methanol and 1.12 g of Dowex 50W-X8 (H+) were added to 1.12 g (3.4431 mmol) of N-glycolylneuraminic acid (NGNA), and the obtained mixture was agitated at room temperature for 20 hours. Since NGNA remained and the reaction was not completed, 150 ml of anhydrous methanol and 2 g of Dowex 50W-X8 (H+) were further added to the reaction solution and, when the mixture was agitated at room temperature for 4 hours, the NGNA was substantially dissolved. The reaction solution was filtered, and the resin was washed with methanol. The filtrate and the washing solution were mixed together and the obtained mixture was subjected to distillation under reduced pressure to obtain 1.08 g of colorless, amorphous crystals (yield, 92%).

The crystals were recrystallized by methanol.

(Physical Properties of Compound (A'))

Melting point: 170°–173° C.
IRγKBr/max cm$^{-1}$:
3400 (—OH, —NH),
1745 (—COOCH$_3$),
1645 (—CONH—),
1550 (—CONH—, amide II)
$^1$H—NMR, ppm/400 MHz (DMSO-d$_6$+D$_2$O, TMS),
1.721 (1H, t, $J_{3ax\ 3eq}$=12.7 Hz, $J_{3ax\ 4}$=11.7 Hz, H$_{3ax}$),
2.050 (1H, dd, $J_{3ax\ 3eq}$=12.7 Hz, $J_{3eq\ 4}$=4.9 Hz, H$_{3eq}$),
3.217 (1H, dd, $J_{7\ 8}$=9.3 Hz, $J_{6\ 7}$=1.0 Hz, H-7),
3.312 (1H, dd, $J_{9\ 9'}$=11.2 Hz, $J_{8\ 9'}$=6.8 Hz, —H—9'),
3.502 (1H, ddd, $J_{7\ 8}$=9.3 Hz, $J_{8\ 9'}$=6.4 Hz, $J_{8\ 9}$=2.5 Hz, H-8),
3.518–3.671 (2H, m, H-9, H-5),
3.714 (3H, s, —COOCH$_3$),
3.845–3.932 (3H, m,

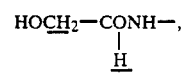

H-6),
3.865 (1H, d, J=16.1 Hz,

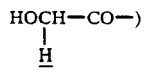

3.911 (1H, d, J=16.1 Hz, HOCH—CO—),
4.034 (1H, ddd, $J_{3ax\ 4}$=11.7 Hz, $J_{4\ 5}$=10.7 Hz, $J_{3eq\ 4}$=4.9 Hz, H-4),
7.813 (1H, d, J=8.8 Hz, —CONH—),
Elementary analysis $C_{12}H_{21}NO_{10}$ 7/10H$_2$O),
MW=351.92 (339.31)
Calculated value: C:40.96, H:6.42, N:3.98,
Measured value C:40.89, H:6.27, N:3.88,

REFERENCE EXAMPLE 2 (PRODUCTION OF COMPOUND (1) FROM COMPOUND (A'))

Production and purification of methyl
5-N-acetoxyacetyl-2,4,7,8-penta-O-acetyl-α,β-D-glycero-D-galacto-2-nonulopyranosonate 1.05 g (3.0945 mmol) of methyl 5-N-glycolyl-3,5-dideoxy-β-D-glycero-D-galacto-2-nonulopyranosonate was dissolved in 15 ml of anhydrous pyridine, 10 ml of anhydrous acetic acid was then added to the obtained solution, and the obtained mixture was agitated at room temperature for 42 hours. The reaction solution was subjected to distillation under reduced pressure, and toluene was then added to the residue. The obtained mixture was subjected to azeotropic distillation (5 times) until no odor of anhydrous acetic acid was generated to obtain 1.846 g of amorphous crystal. 185 g of silica gel which had previously been suspended in chloroform was filled in a column, and the 1.846 g of the amorphous crystals was dissolved in chloroform and then added to the column. Development was performed by using a mixture of chloroform and methanol (50:1) as a developing solvent so that fractions were collected. An eluate was collected every about 15 ml, and each of the fraction solutions was analyzed by TLC so that only the fraction solutions containing the target substance were collected. The solvent was distilled off and the residue was dissolved in water and was lyophilized and then dried under vacuum (P$_2$O$_5$) to obtain 445 mg of a α-substance, 518 mg of β-substance, and 688 mg of a αβ-mixture in a total amount of 1.651 g (theoretical yield, 1.83 g; yield, 90.2%).

(Physical Properties of α-substance)

Melting point: 74°–78° C.
Elementary analysis C$_{24}$H$_{33}$NO$_{16}$2/5H$_2$O
MW=598.74 (591.54)
Calculated value: C:48.14, H:5.69, N:2.34,
Measured value: C:48.12, H:5.57, N:2.38,
IRγkBr/max cm$^{-1}$:
3420 (—NH),
1750 (—COOCH$_3$),
1690 (—CONH—),
1540 (—CONH—, amide II)
$^1$H—NMR ppm/400 MHz (CDCl$_3$, TMS)
2.024 (3H, s, —OCOCH$_3$),
2.039 (3H, s, —OCOCH$_3$),
2.109 (3H, s, —OCOCH$_3$),
2.111 (3H, s, —OCOCH$_3$),
2.130 (3H, s, —OCOCH$_3$),
2.182 (3H, s, —OCOCH$_3$),
2.078 (H$_{3ax}$),
2.571 (1H, dd, J=13.0 Hz, J=4.8 Hz, α-H$_{3eq}$),
3.768 (3H, s, —COOCH$_3$),
4.163 (1H, dd, J=12.3 Hz, J=6.0 Hz, H-9'),
4.175 (1H, ddd, J=10.6 Hz, J=10.4 Hz, J=10.0 Hz, H-5), 4.320 (1H, d, J=15.2 Hz,

4.370 (1H, dd, J=12.3 Hz, J=2.5 Hz, H-9),
4.588 (1H, d, J=15.2 Hz,

4.787 (1H, dd, J=10.6 Hz, J=2.3 Hz, H-6),
5.076 (1H, ddd, J=11.8 Hz, J=10.4 Hz, J=4.8 Hz, H-4),
5.204 (1H, ddd, J=6.4 Hz, J=6.0 Hz, J=2.5 Hz, H-8),
5.334 (1H, dd, J=6.4 Hz, J=2.3 Hz, H-7),
6.197 (1H, d, J=10.0 Hz, —CONH—), (Physical Properties of β-substance)

Melting point: 80°–86° C.
Elementary analysis C$_{24}$H$_{33}$NO$_{16}$7/10H$_2$O,
MW=604.15 (591.54).
Calculated value: C:47.71, H:5.74, N:2.32,
Measured value: C:46.66, H:5.43, N:2.35.
IRβkBr/max cm$^{-1}$:
3400 (—NH),
1750 (—COOCH$_3$),
1700 (—CONH—),
1530 (—CONH—, amide II) $^1$H—NMR ppm/400 MHz (CDCl$_3$, TMS),
2.023 (3H, s, —OCOCH$_3$),
2.043 (3H, s, —OCOCH$_3$),
2.072 (3H, s, —OCOCH$_3$),
2.145 (3H, s, —OCOCH$_3$),
2.168 (3H, s, —OCOCH$_3$),
2.201 (3H, s, —OCOCH$_3$), 2.102 (1H, dd, J=13.4 Hz, J=11.4 Hz, β-H$_{3ax}$),
2.558 (1H, dd, J=13.4 Hz, J=4.7 Hz, β-H$_{3eq}$),
3.799 (3H, s, —COOCH$_3$),
4.103 (1H, ddd, J=10.8 Hz, J=10.2 Hz, J=9.5 Hz, H-5),
4.125 (1H, dd, J=12.3 Hz, J=6.7 Hz, H-9'),
4.188 (1H, dd, J=10.8 Hz, J=2.2 Hz, H-6),
4.302 (1H, d, J=15.3 Hz,

4.490 (1H, dd, J=12.3 Hz, J=2.5 Hz, H-9),
4.614 (1H, d, J=15.3 Hz,

5.080 (1H, ddd, J=5.1 Hz, J=6.7 Hz, J=2.5 Hz, H-8),
5.316 (1H, dd, J=5.1 Hz, J=2.2 Hz, H-7),
5.332 (1H, ddd, J=11.4 Hz, J=10.2 Hz, J=4.7 Hz, H-4),
5.981 (1H, d, J=9.5 Hz, —CONH—),

REFERENCE EXAMPLE 3 (PRODUCTION OF COMPOUND (2) FROM COMPOUND (1))

50 ml of acetyl chloride was added to 340 mg (0.54 mmol) of compound (1) and HCl gas was added to the mixture which was then agitated for one night. Toluene was then added to the reaction solution which was then subjected to distillation (azeotropic distillation).

(Physical Properties)

[α]21/D, −56.6° C., C=0.79, CHCl$_3$,
300 mg (97%)
R$_f$=0.46 (toluene:ethyl acetate=1:2)
NMR: 400 MHz, CDCl$_3$, δ (ppm), TMS,
δ2.039, 2.062, 2.095, 2.123, 2.210 (s, OCOCH$_3$×5),
2.295 (1H, dd, J=11.2, 13.9 Hz, H-3ax),
2.796 (1H, dd, J=4.6, 13.9 Hz, H-3eq),
3.888 (3H, s, —OCH$_3$),
4.074 (1H, dd, J=5.9, 12.5 Hz, H-9),
4.213 (td, J=10.2, 10.5 Hz, H-5),
4.312 (d, J=15.3, —CH$_2$OCO),
4.414 (1H, t, J=2.9, H-6),
4.443 (1H, dd, J=2.7, 5.4 Hz, H-9),
4.629 (1H, d, J=15.3 Hz, —CH$_2$OCO—),
5.182 (td, J=2.4, 10.0 Hz, H-8),
5.431 (1H, dd, J=2.2, 6.8 Hz, H-7),
5.469 (1H, m, H-4),
6.068 (d, J=10.0 Hz, NH),

REFERENCE EXAMPLE 4 (PRODUCTION OF COMPOUNDS (3) AND (4) FROM COMPOUND (2))

(A) 1.4 g (1.6 mmol) of compound (B), 1.125 g (4.5 mmol) of Hg(CN)$_2$, 540 mg (1.5 mmol) of HgBr$_2$, and 2 ml of dichloroethane were added to 1.5 g of activated Molecular Sieves 4A, and the obtained mixture was agitated for 1 hour. 500 mg (0.8 mmol) of compound (2) which had been dissolved in 4 ml of dichloroethane under ice-MeOH cooling was then added to the mixture, which was then agitated for one night. After being agitated at 70° C. for one day, the reaction solution was filtered by using Celite, and ethyl acetate was added to the filtrate. An organic layer was washed with an aqueous NaHCO$_3$ solution, water, and saturated salt water, dried with anhydrous MgSO$_4$, and then subjected to distillation. The residue was purified by column chromatography (C-300, 80 g; toluene:ethyl acetate=2:1 and then 1:2) to obtain 195.8 mg of compound (3) (yield, 17.3%) and 81 mg of compound (4) (yield, 7.2%).

(B) 3 g (3.4 mmol) of compound (B), 750 mg (3 mmol) of Hg(CN)$_2$, 1.08 g (3 mmol) of HgBr$_2$, and 5 ml of dichloroethane were added to 3 g of activated Molecular Sieves 4A, and the mixture was agitated for 1 hour. 1 g (1.6 mmol) of compound (2) which had been dissolved in 7 ml of dichloroethane under ice-MeOH cooling was then added to the mixture, which was then agitated for one night. After being agitated at 70° C. for one day, the reaction solution was filtered by using Celite, and ethyl acetate was added to the filtrate. An organic layer was washed with an aqueous NaHCO$_3$ solution, water, and saturated salt water, dried with anhydrous MgSO$_4$, and then subjected to distillation. The residue was purified by column chromatography (C-300, 200 g; toluene:ethyl acetate=2:1, then 1:2) to obtain 408 mg of compound (3) (yield, 18.1%) and 165 mg of compound (4) (yield, 7.3%).

(C) 755 mg (1 mmol) of compound (B) which had been dissolved in 2.5 ml of THF and 144 mg (0.55 mmol) of AgOTf were added to 1 g of activated Molecular Sieves 4A, and the mixture was agitated at −10° C. for 30 minutes. 300 mg (527 μmol) of compound (2) which had been dissolved in 2.5 ml of THF was then added to the mixture, which was then agitated at room temperature for one night. After being agitated at 70° C. for one day, the reaction solution was subjected to Celite filtration, and ethyl acetate was then added to the filtrate. An organic layer was washed with an aqueous NaHCO$_3$ solution, water, and saturated salt water, dried with anhydrous MgSO$_4$, then subjected to distillation. The residue was purified by column chromatography (C-300, 50 g; toluene : ethyl acetate=2:1, then 1:2) to obtain 23.8 mg of compound (3) (yield, 3.5%) and 26.7 mg of compound (4) (yield, 3.9%).

(Physical Properties)

Compound (3)

$R_f$=0.574 (toluene:ethyl acetate=1:2) $[\alpha]23/D$, −3.57, (C=1.10, CHCl$_3$) Elementary analysis,
Theoretical value: C:64.53, H:6.20, N:0.99,
Measured value C:64.48, H:6.13, N:0.72,
NMR: 400 MHz ppm (TMS),
1.913, 1.966, 2.044, 2.103, 2.183 (s, OCOCH$_3$×5),
2.555 (1H, dd, J=4.6, 13.4 Hz, H-3c),
3.618 (s, OCH$_3$),
5.259 (1H, td, J=2.4, 8.7 Hz, H-8c),
0 5.297 (1H, t, J=2.4 Hz),
5.333 (1H, ddd, J=4.6, 10.9, 10.9 Hz, H-4c),
5.585 (1H, d, J=10.2, NH),
7.21–7.37 (30H, m, benzyl group×6).
$^{13}$C NMR, CDCl$_3$, ppm, 99.69 (C-2c), 102.29 (C-1a), 102.40 (C-1b)

Compound (4)

$R_f$=0.479 (toluene:ethyl acetate=1:2)
$[\alpha]23/D$, −7.12 (C=1.25, CHCl$_3$)
Elementary analysis:
Theoretical value: C:64.53, H:6.20, N:0.99,
Measured value: C:64.15, H:6.26, N:1.02.
NMR: 400 MHz ppm (TMS),
1.883, 1.984, 2.001, 2.100, 2.189 (s, OCOCH$_3$×5),
2.521 (1H, dd, J=4.6, 13.1 Hz, H-3ceq),
3.774 (1H, m, —OCH$_3$),
4.20 (1H, m, H-4c),
5.261 (1H, dd, J=1.7, 8.0 Hz, H-7),
5.416 (1H, m, H-8),
5.808 (1H, d, J=9.7, NH),
7.20–7.40 (30H, m, benzyl group×6),
$^{13}$C NMR, 22.5 MHz, CDCl$_3$ ppm ,
99.69 (C-2c), 103.75 (C-1a), 103.91 (C-1b).

REFERENCE EXAMPLE 5 (PRODUCTION OF COMPOUND (5) FROM COMPOUND (3))

5 ml of pyridine and 5 ml of anhydrous acetic acid were added to 144 mg (101.8 μmol) of compound (3), and the mixture was agitated at 60° C. for one night. The reaction solution was dried up as it was.

148 mg (99.8%)
$R_f$=0.397 (toluene:ethyl acetate=1:1)
$[\alpha]D/24$, −13.30 (C=1.0, CHCl$_3$)
Elementary analysis:
Theoretical value: C:64.32, H:6.16, N:0.96:
Measured value C:64.66, H:6.17, N:1.09,
$^1$H NMR 400 HMz ppm CDCl$_3$ (TMS),
1.819, 1.962, 2.034, 2.106, 2.143, 2.169, (s, OCOCH$_3$×6),
2.571 (1H, dd, J=4.6, 13.1 Hz, H-3ceq),
3.444 (3H, s, OCH$_3$),
4.095 (1H, td, J=10.5, 10.5 Hz),
5.101 (1H, m, H-4c),
5.378 (1H, d, J=3.2 Hz, H-4b),
7.23–7.38 (30H, m, benzoyl group×6),
$^{13}$C NMR, ppm CDCl$_3$, 99.25 (C-2c), 101.86 (C-1a), 102.34 (C-1b)

REFERENCE EXAMPLE 6 (PRODUCTION OF COMPOUND (7) FROM COMPOUND (5))

390 mg (267.7 μmol) of compound (5) was dissolved in 50 ml of methanol, 200 mg of 10% Pd-C200 was added to the methanol solution, and the obtained mixture was subjected to catalytic reduction at room temperature for one night. The reaction solution was filtered by Celite and then dried up.

232 mg (94.7%)
$R_f$=0.632 (BuOH:EtOH:H$_2$O=2:1:1)
$[\alpha]D/24+20.32$ (C=1.08, methanol)
Elementary analysis:
Theoretical value: C:47.22, H:5.83, N:1.53,
Measured value: C:47.25, H:5.77, N:1.78

REFERENCE EXAMPLE 7 (PRODUCTION OF COMPOUND (9) FROM COMPOUND (7))

8 ml of pyridine and 8 ml of anhydrous acetic acid were added to 220 mg (240.2 μmol) of compound (7), and the obtained mixture was agitated at room temperature for three days. The reaction solution was subjected to distillation and the residue was purified by column chromatography (C-300, 20 g; toluene : ethyl acetate=1:5).

247 mg (88%)
$R_f$=0.833 (CHCHl$_3$:MeOH=10:0.5)
$[\alpha/D/24+12.43$ (C=1.0, CHCHCl$_3$)
Elementary analysis:
Theoretical value: C:49.63, H:5.61, N:1.20,
Measured value: C:49.94, H:5.61, N:1.20

REFERENCE EXAMPLE 8 (PRODUCTION OF COMPOUND (11) FROM COMPOUND (9))

220 mg (188 μmol) of compound (9) was dissolved in 2 ml of DMF, 24 mg (240 μmol) of H$_2$NNH$_2$ AcOH was added to the obtained solution, and the obtained mixture was agitated at 60° C. for 20 minutes. Ethyl acetate was added to the reaction solution, and an organic layer was washed with water and saturated salt water, dried with anhydrous MgSO$_4$, and subjected to distillation. The residue was purified by column chromatography (C-300, 20 g; acetone : CCl$_4$=1:2). 144 mg (68%)

R$_f$=0.58 (acetone:CCl$_4$=1:1)
[αD/23+17.40 (C=0.52, CHCl$_3$)
Elementary analysis:
Theoretical value: C:49.07, H:5.64, N:1.24,
Measured value: C:48.88, H:5.67, N:1.44

REFERENCE EXAMPLE 9 (PRODUCTION OF COMPOUND (13) FROM COMPOUND (11))

140 mg (124 μmol) of compound (11) was dissolved in 1 ml of dichloromethane, 358 μl (3.57 mmol) of Cl$_3$CCN and 18 1 (0.126 mmol) of DBU were added to the obtained solution at 0° C., and the obtained mixture was agitated for 4 hours as it was. The reaction solution was purified by column chromatography (C-300, 18 g; acetone :-CCl$_4$=1:2). 120 mg (76%)

R$_f$=0.367 (acetone : CCl$_4$=1:2) [α]D/24+26.98 (C=0.825, CHCl$_3$)
Elementary analysis:
Theoretical value : C:45.35, H:5.07, N.2.20,
Measured value: C:45.61, H:5.04, N:2.30
$^1$H MNR CDCl$_3$ ppm TMS,
1.982, 2.017, 2.043, 2.061, 2.062, 2.069, 2.083, 2.117, 2.152, 2.185, 2.304 (s, OCOCH$_3$×11),
1.777 (1H, t, J=12.2 Hz, H-3cax), 2.436 (1H, dd, J=4.6, 13.4 Hz, H-3ceq),
3.840 (s, OCH$_3$),
4.349 (1H, d, J=15.6 Hz, AcOCH$_2$—CO—),
4.601 (1H, d, J=15.3 Hz, AcOCH$_2$—CO—),
5.043 (1H, m, H-4c),
5.297 (1H, d, J=2.9 Hz, H-4b),
5.533 (1H, t, J=9.7 Hz, H-3a),
6.313 (1H, d, J=10.2 Hz, NH),
6.474 (1H, d, J=3.6 Hz, H-1a),
$^{13}$C NMR, CDCl$_3$, ppm,
93.19 (C-1a), 99.63 (C-2c), 101.15 (C-1b)

REFERENCE EXAMPLE 10 (PRODUCTION OF COMPOUND (15) FROM COMPOUND (13))

100 mg (78.6 μmol) of compound (13) and 70 mg (78.8 μmol) of compound (C) which had been dissolved in 3 ml of dichloromethane were added to 1.5 g of activated Molecular Sieves AW-300, 15 μl (124 μmol) of BF$_3$ Et$_2$O was added to the obtained mixture under ice-MeOH cooling, and the obtained mixture was agitated for one night at it was. The reaction solution was filtered by Celite, subjected to distillation, and then purified by column chromatography (C-300, 25 g; toluene:ethyl acetate=1:1).

90.6 mg (58%)
R$_f$=0.229 (toluene:ethyl acetate=1:1)
[αD/−11.86 (C=0.42, CHCl$_3$)
$^1$H NMR CDCl$_3$ ppm TMS,
0.881 (6H, t, J=7.0 Hz, —CH$_2$CH$_3$),
0.997 (9H, s, —CH$_3$×3),
1.251 (s, —CH$_2$—),
1.960, 1.981, 2.032, 2.042, 2.052, 2.060, 2.070, 2.088, 2.150, 2.181, 2.302 (s, OCOCH$_3$×11),
2.434 (1H, dd, J=4.6, 13.4 Hz, H-4ceq),
3.841 (3H, s, OCH$_3$),
4.350 (1H, d, J=15.3 Hz),
4.598 (1H, d, J=15.3 Hz, —OCH$_2$CONH),
5.041 (1H, m, H-4c),
5.291 (1H, d, J=2.5 Hz),
7.31–7.40 (6H, m, aromatic proton),
7.61–7.76 (4H, m, aromatic proton),

REFERENCE EXAMPLE 11 (PRODUCTION OF COMPOUND (17) FROM COMPOUND (15))

20 mg (10 μmol) of compound (15) was dissolved in 1 ml of THF, 11.2 μ(11 μmol) of Bu$_4$NF was added to the obtained solution, and the obtained mixture was agitated at room temperature for 1 hour. 39.7 μg (39 μmol) of Bu$_4$NF was added to the obtained mixture which was then agitated for two days. The reaction solution was subjected to distillation, 1 ml of pyridine and 1 ml of anhydrous acetic acid were added to the residue, and the obtained mixture was agitated at 60° C. for 6 hours. The reaction solution was subjected to distillation and purified by column chromatography (C-300, 3 g; CHCl$_3$ MeOH=10:0.2).

17 mg (94%)
R$_f$=0.70 (CHCl$_3$:MeOH=10:0.25)
[αD/−5.33 (C=0.90, CHCl$_3$)
Elementary analysis:
Theoretical value(1H$_2$O), C:59.45, H:8.21, N:1.54,
Measured value: C:59.05, H:7.95, N:1.72
$^1$H NMR CDCl$_3$ ppm TMS 400 MHz,
0.880 (6H, t, J=6.5 Hz, —CH$_2$CH$_3$×2),
1.252 (s, —CH$_2$×32),
1.771 (1H, t, J=12.2 Hz. H-3cex),
1.981, 2.004, 2.040, 2.042, 2.053, 2.060, 2.066, 2.086, 2.150, 2.159, 2.222, 2.295 (s, OCOCH$_3$×-12),
2.438 (1H, dd, J=4.6, 12.1 Hz, H-3ceq),
3.840 (3H, s, OCH$_3$),
4.349 (1H, d, J=15.6 Hz, —OCH$_2$CONH)

EXAMPLE 1 (PRODUCTION OF COMPOUND (19) FROM COMPOUND (17))

16 mg (8.3 μmol) of compound (17) was dissolved in 1.5 ml of methanol, 1 ml of 0.1N NaOCH$_3$ was added to the obtained solution, and the obtained mixture was agitated at room temperature for 6 hours. The reaction solution was dried up, 1 ml of MeOH, 1 ml of THF, and 0.5 ml of H$_2$O were added to the residue, and the obtained mixture was agitated at room temperature for one night. The reaction solution was neutralized by Amberlite IRC-50, filtered, and then purified by Sephadex LH-20 (eluted with CHCl$_3$:MeOH:H$_2$O=5:3:0.46). 10.8 mg (94%)

R$_f$=0.25 (BuOH:EtOH:H$_2$O=2:1:1)
[α]D/26 —7.60 (C=0.50, CHCl$_3$: MeOH=1:1)
NMR 400 MHz d 6DMSO-D$_2$O (98:2) TMS ppm,
0.854 (6H, t, J=6.5 Hz, —CH$_2$CH×2),
1.240 (64H, s, —CH$_2$—×32),
2.041 (2H, t, J=7.0 Hz, H-2cer),
1.934 (2H, m, H-6cer),
3.057 (1H, t, J=8.0 Hz, H-2a),
4.176 (1H, d, J=7.57 Hz, H-1a),
4.193 (1H, d, J=6.1 Hz, H-1b),
5.372 (1H, dd, J=6.8, 15.3 Hz, H-4cer),
5.557 (1H, t, J=15.3, 6.6 Hz, H-5cer),

REFERENCE EXAMPLE 13 (PRODUCTION OF COMPOUND (6) FROM COMPOUND (4))

5 ml of pyridine and 5 ml of anhydrous acetic acid were added to 81 mg (57.2 μmol) of compound (4), and the obtained mixture was agitated at 60° C. for one night. The reaction solution was dried up as it was. 84 mg (100%)

$R_f$=0.269 (toluene:ethyl acetate=1:1)
$[\alpha]D/24$ −13.13 (C=0.515, CHCl$_3$)
Elementary analysis:
Theoretical value C:64.32, H:6.16, N:0.96,
Measured value: C:64.02, H:6.00, N:1.08 NMR 400 MHz, ppm, CDCl$_3$, TMS,
1.749, 1.971, 1.997, 2.000, 2.123, 2.185, (s, OCOCH$_3$×6),
1.851 (1H, t, J=12.4 Hz, H-3cax),
2.616 (1H, dd, J=4.6, 12.7 Hz, H-3ceq),
4.103 (1H, q, J=10.5 Hz, H-5c),
5.049 (1H, d, J=2.9 Hz, H-4b),
5.598 (1H, m, H-8c),
5.779 (1H, d, J=10.2 Hz, NH),
7.17–7.39 (30H, m, benzyl group×6)

REFERENCE EXAMPLE 14 (PRODUCTION OF COMPOUND (8) FROM COMPOUND (6))

232 mg (159.2 μmol) of compound (6) was dissolved in 50 ml of methanol, 150 mg of 10% Pd-C was added to the obtained solution, and the obtained mixture was subjected to catalytic reduction at room temperature for one night. The reaction solution was filtered by Celite and then dried up. 141 mg (97.2%)

$R_f$=0.632 (BuOH: EtOH: H$_2$O=2:1:1)
$[\alpha]24$+24.52 (C=0.50, methanol)
Elementary analysis:
Theoretical value C:46.30, H:5.94, N:1.50, (containing 1H$_2$O)
Measured value: C:46.53, H:5.82, N:1.86

REFERENCE EXAMPLE 15 (PRODUCTION OF COMPOUND (10) FROM COMPOUND (8))

8 ml of pyridine and 8 ml of anhydrous acetic acid were added to 130 mg (141.9 μmol) of compound (8), and the obtained mixture was agitated at room temperature for three days. The reaction solution was subjected to distillation and then purified by column chromatography (C-300, 20 g; toluene: ethyl acetate=1:5). 151 mg (95%)

$R_f$=0.743 (CHCl$_3$: MeOH=10:0.5)
$[\alpha]D/24$ +11.17 (C=0.60, CHCl$_3$)
Elementary analysis:
Theoretical value: C:49.36, H:5.61, N:1.20,
Measured value: C:49.21, H:5.63, N:1.54

REFERENCE EXAMPLE 16 (PRODUCTION OF COMPOUND (12) FROM COMPOUND (10))

140 mg (120 μmol) of compound (10) was dissolved in 2 ml of DMF, 15 mg (160 μmol) of H$_2$NNH$_2$ AcOH was added to the obtained solution, and the obtained mixture was agitated at 60° C. for 25 minutes. Ethyl acetate was added to the reaction solution, and an organic layer was washed with water and saturated salt water, dried with anhydrous MgSO$_4$, and then subjected to distillation. The residue was purified by column chromatography (C-300, 20 g; acetone: CCl$_4$=1:2). 133 mg (98%)

$R_f$=0.549 (acetone: CCl$_4$=1:1)
$[\alpha]D/23$+14.26 (C=0.70, CHCl$_3$)

Elementary analysis: Theoretical value: C:49.07, H:5.64, N:1.24,
Measured value: C:48.79, H:5.70, N:1.70

REFERENCE EXAMPLE 17 (PRODUCTION OF COMPOUND (14) FROM COMPOUND (12))

116 mg (103 μmol) of compound (12) was dissolved in 1 ml of dichloromethane, 358 μl (3.53 mmol) of Cl$_3$CCN and 15 μl (0.11 mmol) of DBU were added to the obtained solution, and the obtained mixture was agitated for 4 hours as it was. The reaction solution was purified by column chromatography (C-300, 20 g; acetone: CCl$_4$=1:2). 121 mg (92%)

$R_f$=0.278 (acetone: CCl$_4$=1:2)
$[\alpha]D/24$+34.0 (C=0.25, CHCl$_3$)
Elementary analysis:
Theoretical value: C:44.40, H:5.20, N:1.16, (containing 1.5H$_2$O),
Measured value: C:44.14, H:4.80, N:2.52,
NMR 400 MHz CDCl$_3$, ppm, TMS, 1.992, 2.012, 2.054, 2.073, 2.075. 2.084, 2.100, 2.180, 2.186 (s, OCOCH$_3$×11),
1.683 (1H, t, J=12.4 Hz, H-3cax),
2.604 (1H, dd, J=4.6, 12.7 Hz, H-3ceq),
3.869 (3H, s, OCH$_3$),
4.274 (1H, d, J=15.1 Hz, —OCOCH$_2$O—),
4.571 (1H, d, J=15.3 Hz, —OCOCH$_2$O—),
4.513 (1H, dd, J=3.4, 10.0 Hz, H-2a),
4.664 (1H, d, J=8.0 Hz, H-1b),
4.899 (1H, d, J=2.6 Hz, H-4b),
4.975 (1H, m, H-4c),
4.962 (1H, dd, J=7.8, 10.0 Hz, H-2b),
5.081 (1H, dd, J=3.9, 10.2 Hz, H-3b),
5.373 (1H, dd, J=2.6, 9.2 Hz, H-7c),
5.500 (1H, m, H-8c),
5.553 (1H, t, J=9.7 Hz, H-3m),
5.779 (1H, d, J=10.0 Hz, —CONH—),
6.492 (1H, d, J=3.6 Hz, H-1a),
8.649 (1H, s, =NH),

REFERENCE EXAMPLE 18 (PRODUCTION OF COMPOUND (16) FROM COMPOUND (14))

80 mg (62.9 μmol) of compound (14) and 70 mg (78.8 mol) of compound (C) which had been dissolved in 3 ml of dichloroethane were added to 1.5 g of activated Molecular Sieves AW-300, 15 μl (124 μmol) of BF$_3$ Et$_2$O was added to the obtained mixture under ice-MeOH cooling after 30 minutes, and the obtained mixture was agitated for one night as it was. The reaction solution was filtered by Celite and then subjected to distillation. The residue was purified by column chromatography (C-300, 25 g; toluene:ethyl acetate=1:1). 65.4 mg (52%)

$R_f$=0.131 (toluene:ethyl acetate: 1:1)
$[\alpha]_D{}^{24}$ −11.43 (C=0.35, CHCl$_3$)
Elementary analysis:
Theoretical value: C: 62.54, H: 8.23, N: 1.40, Measured value: C: 62.49, H: 8.15, N: 1.59.
NMR 400 MHz CDCl$_3$ ppm TMS, 0.878 (3H, t, J=5.8 Hz, —CH$_2$CH$_2$), 0.881 (3H, t, J=5.6 Hz, —CH$_2$CH$_2$), 0.993 (9H, s, +Butyl group), 1.251 (64H, s, —CH$_2$—×32), 1.961, 1.992, 2.013, 2.043, 2.073, 2.075, 2.083, 2.601 (1H, dd, J=4.6, 12.9 Hz, H—3eq), 3.867 (3H, s, OCH$_3$), 4.275 (1H, d, J=15.3 Hz, —OCH$_2$COCH$_3$), 4.570 (1H, d, J=15.3 Hz, —OCH$_2$COCH$_3$), 4.428 (1H, d, J=8.0 Hz, H—1a), 4.640 (1H, d, J=8.0 Hz, H—1b), 4.950 (1H, m, H—-4c), 5.500 (1H, m, H—8c), 5.773 (1H, d, J=10.0 Hz, NH), 7.30-7.42 (6H, m, benzene ring), 7.60-7.70 (4H, m, benzene ring)

REFERENCE EXAMPLE 19 (PRODUCTION OF COMPOUND (18) FROM COMPOUND (16))

24 mg (12 μmol) of compound (16) was dissolved in 2 ml of THF, 60 μl (59 μmol) of Bu$_4$NF was added to the obtained solution, and the obtained mixture was agitated at room temperature for one night. The reaction solution was dried up, 1 ml of pyridine and 1 ml of anhydrous acetic acid were added to the residue, and the obtained mixture was agitated at 40° C. for one night. The reaction solution was subjected to distillation and purified by column chromatography (C-300, 10 g; CHCl$_3$: MeOH=10 : 0.2).

14 mg (64%)

R$_f$=0.48 (CHCl$_3$: MeOH=10:0.25)

$[\alpha]_D^{26}$ −9.0 (C=0.70, CHCl$_3$)

NMR 400 MHz CDCl$_3$ ppm TMS, 0.880 (6H, t, J=7.0 Hz, —CH$_2$CH$_3$×2), 1.252 (64H, s, —CH$_2$—), 1.682 (1H, t, J=12.4 Hz, H-3cax) 1.991, 2.006, 2.037, 2.041, 2.076, 2.081, 2.090, 2.108, 2.179, 2.184, 2.239 (s, OCOCH$_3$×12), 2.599 (1H, dd, J=4.6, 12.6 Hz), 3.866 (3H, s, OCH$_3$), 5 4.274 (1H, d, J=15.3 Hz, —OCH$_2$CO—), 4.425 (1H, d, J=8.0 Hz, H—1a), 4.570 (1H, d, J=15.3 Hz, —OCH$_2$CO—), 4.660 (1H, d, J=8.0 Hz, H—1b), 5.520 (1H, m, H—8c)

EXAMPLE 2 (PRODUCTION OF COMPOUND (20) FROM COMPOUND (18))

2 mg (6.6 μmol) of compound (18) was dissolved in ml of MeOH, 1 ml of 0.1N NaOCH$_3$ was added to the obtained solution, and the obtained mixture was agitated at room temperature for one night. The reaction solution was subjected to distillation, 1 ml of MeOH, 1 ml of THF, and 0.5 ml of H$_2$O were added to the residue, and the obtained mixture was agitated at room temperature for one night. The reaction solution was neutralized by Amberlite IRC-50, filtered, and then purified by Sephadex LH-20 (eluted with CHCl$_3$:MeOH: H$_2$O=5:3:0.46).

8.5 mg (97%)

R$_f$=0.25 (BuOH:EtOH:H$_2$O=2:1:1)

$[\alpha]_D^{26}$ −0.94 (C=0.425, CHCl$_3$: MeOH=1:1)

NMR 400 MHz d-6 DMSO-D20(98:2) TMS ppm, 0.852 (6H, t, J=6.3 Hz, —CH$_2$CH$_3$×2), 1.232 (64H, s, —CH$_2$—) 1.930 (2H, m, H—6cer), 2.026 (2H, t, J=7.3 Hz, H—2cer), 2.757 (1H, dd, J=5.1, 11.9 Hz, H—3ceq), 3.041 (1H, t, J=8.5 Hz, H—2a), 4.159 (1H, d, J=7.8 Hz, H—1a), 4.200 (1H, d, J=7.8 Hz, H—1b), 5.343 (1H, dd, J=7.3 Hz, H—4cer), 5.534 (1H, td, J=14.9, 6.8 Hz, H—5cer)

REFERENCE EXAMPLE 20 (PRODUCTION OF COMPOUND (22) FROM COMPOUND (21))

1.360 g (2.09 mmol) of ceramide (21) was dissolved in 30 ml of pyridine, 722.8 mg (2.77 mmol) of TrCl was added to the obtained solution, and the obtained mixture was agitated at 50° C. for one night. The reaction solution was subjected to distillation, chloroform was added to the residue so as to dissolve it, and a chloroform layer was washed with water and saturated salt water, dried with anhydrous MgSO$_4$, and subjected to distillation. The residue was purified by column chromatography (Wakogel C-300, 85 g; toluene : ethyl acetate=5:1; containing Et$_3$N) to obtain 909 mg of compound (22) (45%).

(Physical Properties of Compound (22))

R$_f$=0.435 (toluene: ethyl acetate=5:1)

$[\alpha]_D^{23}$ +2.24 (C=0.75, EtOAc)

EXAMPLE 3 (PRODUCTION OF COMPOUND (23) FROM COMPOUND (22))

15 ml of DMF, 370 mg (1.36 mmol) of Ph$_2$tBuSiCl, and 183 mg (2.688 mmol) of imidazole were added to 800 mg (896.4 μmol) of compound (22), and the obtained mixture was agitated at room temperature for one night. Ether was added to the reaction solution, and an ether layer was washed with water and saturated salt water, dried with anhydrous MgSO$_4$, and subjected to distillation. The residue was purified by column chromatography (Wakogel C-300, 80 g; hexane:ethyl acetate=10:1, containing Et$_3$N) to obtain 1.006 g of compound (23) (99%).

(Physical Properties of Compound (23))

R$_f$=0.57 (hexane:ethyl acetate=5:1)

$[\alpha]_D^{25}$ +8.38 (C=1.60, EtOAc)

NMR 400 MHz CDCl$_3$ ppm TMS c, 0.880 (6H, t, J=5.8 HZ, —CH$_2$CH$_3$×2), 0.949 (9H, s, tBu group), 1.253 (62H, s, —CH$_2$—), 20 1.472 (2H, m, H—3$^1$), 1.749 (2H, td, J=4.7, 6.3 Hz, H—6), 1.884 (2H, t, J=7.2 Hz, H—21), 3.146 (1H, dd, J=5.3, 9.2 Hz, H—1), 3.298 (1H, dd, J=5.8, 9.2 Hz, H—1), 4.270 (1H, m, H—2), 4.386 (1H, t, J=4.8, H—3), 5.278 (1H, d, J=13.6 Hz, —NH), 7.192-7.605 (25H, m, benzene ring)

EXAMPLE 4 (PRODUCTION OF COMPOUND (24) FROM COMPOUND (23))

1.0 g (883.4 μmol) of compound (23) was dissolved in a mixture of 20 ml of dichloroethane and 1 ml of methanol, 67 mg (352.2 μmol) of TsOH was added to the resultant solution, and the obtained mixture was agitated at room temperature for 1 hour. The reaction solution was neutralized by adding a saturated NaHCO$_3$ solution thereto, and chloroform was added to the reaction solution. A chloroform layer was washed with water and saturated salt water, dried with anhydrous MgSO$_4$, and then subjected to distillation. The residue was purified by column chromatography (Wakogel C-300, 25 g; hexane : ethyl acetate=5:1) to obtain 650 mg of compound (24) (83%).

(Physical Properties of Compound (24))

R$_f$=0.113 (hexane : ethyl acetate=5:1)

$[\alpha]_D^{25}$ 13.79 (C=0.425, EtOAc)

NMR 400 MHz CDCl$_3$ ppm TMS, 0.879 (6H, t, J=6.5 HZ, —CH$_2$CH$_3$×2), 1.066 (9H, s, tButyl group), 1.252 (62H, s, —CH$_2$—), 1.574 (2H, m, H—31), 1.869 (2H, m, H—6), 1.962 (2H, m, H—2), 3.621 (1H, ddd, J=2.9, 7.2, 11.0 Hz, H—1), 3.831 (1H, m, H—2), 3.887 (1H, ddd, J=2.6, 4.4, 11.1 Hz, H—1) , 4.335 (1H, t, J=3.6, H—3), 5.370 (1H, dd, J=15.2, 5.5 Hz, H—4), 5.406 (1H, dt, J=15.2, 5.6, H—5), 7.34-7.66 (10H, m, benzene ring)

EXAMPLE 5 (PRODUCTION OF COMPOUND (25) FROM COMPOUND (22))

10 ml of DMF was added to 280 mg (313.7 μmol) of compound (22), 82.4 mg (387 μmol) of Me$_2$(CMe$_2$Ph)SiCl and 54 mg of imidazole were added to the resultant mixture, and the obtained mixture was agitated at room temperature for one night. Ether and water were added to the reaction solution so that ether extraction is performed, and an ether layer was washed with water and saturated salt water, dried with anhydrous MgSO₄, then subjected to distillation to obtain 480 mg of compound (25).

(Physical Properties of Compound (25))

$R_f$=0.532 (hexane:ethyl acetate=5:1)

EXAMPLE 6 (PRODUCTION OF COMPOUND (26) FROM COMPOUND (25))

480 mg of compound (26) was dissolved in a mixture of 10 ml of CH₂Cl₂ and 1 ml of CH₃OH, 60 mg of TsOH was added to the resulting solution, and the obtained mixture was agitated at room temperature for 6 hours. Sodium bicarbonate was added to the reaction solution, which was then subjected to extraction with CHCl₃. A CHCl₃ layer was washed with water and saturated salt water, dried with anhydrous MgSO₄, then subjected to distillation. The residue was subjected to decantation with ether, and an ether solvent was distilled off. The residue was purified by a silica gel column (C-300, 35 g; hexane:EtOAc=5:1) to obtain 61 mg of Compound (26) (20.5%).

(Physical Properties of Compound (26))

$R_f$=0.08 (hexane:ethyl acetate=5:1)
$[\alpha]_D^{26}$ −4.367 (C=0.60, CHCl₃)

EXAMPLE 7 (PRODUCTION OF COMPOUND (27) FROM COMPOUND (22))

280 mg (313.7 μmol) of compound (22) was dissolved in 10 ml of DMF, 130 mg (387 μmol) of Ph₂(CMe₂Ph)SiCl and 54 mg of imidazole were added to the resultant solution, and the obtained mixture was agitated at room temperature for one night, then at 40° C. for one night. The reaction solution was subjected to ether extraction, and an ether layer was washed with water and saturated salt water, dried with anhydrous MgSO₄, then subjected to distillation. The residue was purified by using a silica gel column (C-300, 20 g; hexane:ethyl acetate=5:1) to obtain 410 mg of Compound (27).

(Physical Properties of compound (27))

$R_f$=0.534 (hexane:ethyl acetate=5:1)

EXAMPLE 8 (PRODUCTION OF COMPOUND (28) FROM COMPOUND (27))

(I) 410 mg of compound (27) was dissolved in a mixture of 10 ml of CH₂Cl₂ and 1 ml of CH₃OH, 30 mg of TsOH was added to the resultant solution, and the obtained mixture was agitated at room temperature for 1 hour. Sodium bicarbonate was added to the reaction solution, which was then subjected to extraction with CHCl₃. An organic layer was washed with water and saturated salt water, dried with anhydrous MgSO₄, then subjected to distillation. The residue was subjected to decantation with ether, and the ether solvent was distilled off. The residue was purified by using a silica gel column (C-300, 20 g; hexane:ethyl acetate=5:1) to obtain 130 mg of compound (28) (43.6% from compound (22)).

(Physical Properties of Compound (28))

$R_f$=0.128 (hexane:ethyl acetate=5:1)
$[\alpha]_D^{26}$ −11.11 (C=1.08, CHCl₃)

(II) 4 ml of ether and 6 ml of formic acid were added to 60 mg of compound (27), and the obtained mixture was agitated at room temperature for 1 hour. An aqueous sodium bicarbonate and ether were added to the reaction solution so that extraction was performed. An ether layer was washed with water and saturated salt water, dried with anhydrous MgSO₄, then subjected to distillation. The residue was purified by a silica gel column (C-300, 20 g; hexane : ethyl acetate=5:2) to obtain 10 mg of compound (28) (20%).

We claim:

1. A compound of the formula

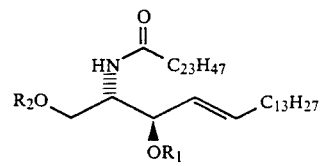

wherein $R_1$ is hydrogen or $SiR_3R_4R_5$ wherein $R_3$ and $R_4$ are each methyl or phenyl, $R_5$ is tertiary butyl or dimethylphenylmethyl, and $R_2$ is hydrogen, trityl, or

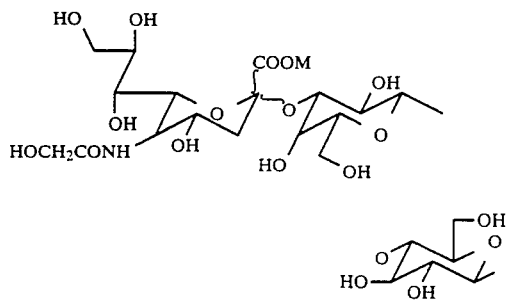

wherein M is an alkali metal atom.

2. The compound according to claim 1, which is

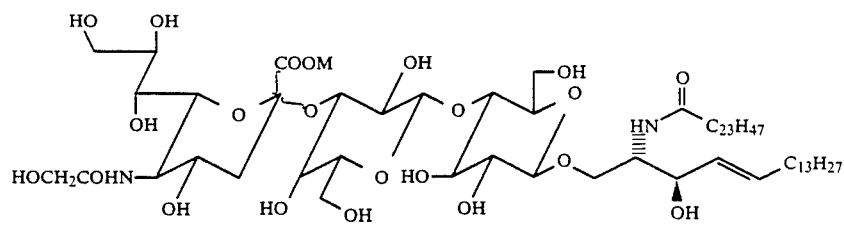

wherein T is an alkali metal atom.

3. A process of producing ganglioside-related compounds which comprises hydrolyzing a compound of the formula

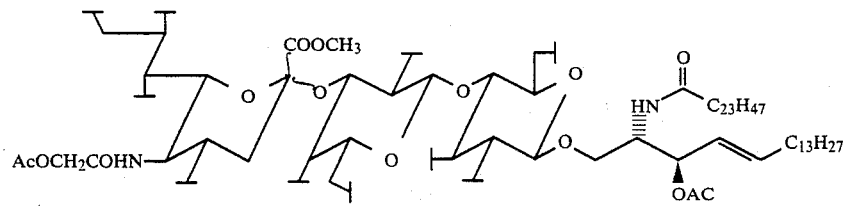

wherein  is OCOCH₃ and Ac is COCH₃ to produce a compound of the formula

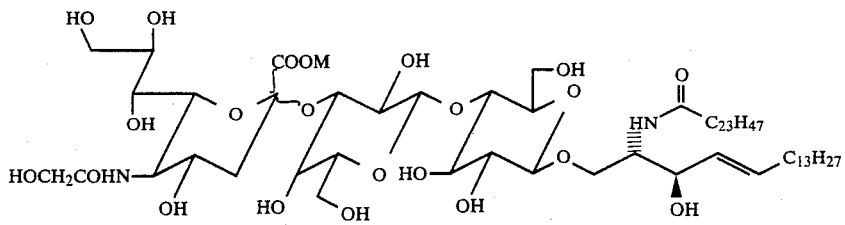

wherein M is an alkali metal atom.

4. The process according to claim 3, wherein said hydrolyzing is carried out by first deacylating said compound

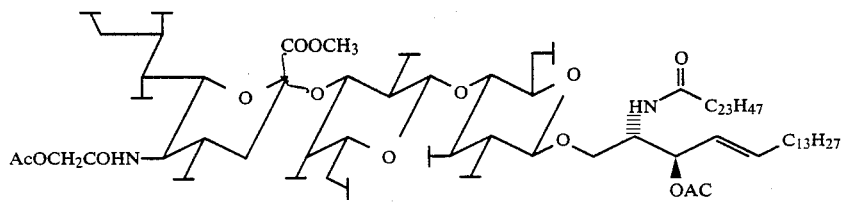

wherein  is OCOCH₃ and Ac is COCH₃ using a catalyst selected from the group consisting of sodium hydride-methanol, potassium carbonate-methanol, potassium hydroxide-methanol and sodium hydroxide-methanol, and then reacting the deacylated compound thus obtained with a catalyst selected from the group consisting of NaOH, KOH and LiOH.

5. The process according to claim 4, wherein said deacylation is carried out in a solvent selected from the group consisting of methanol, ethanol, propanol and tetrahydrofuran and dioxane.

6. The process according to claim 5, wherein said deacylation is carried out at a reaction temperature of from about −10° C. to about 50° C. and a reaction time of from about 30 minutes to 24 hours.

7. The process according to claim 4, wherein said deacylated compound is reacted with said NaOH, KOH or LiOH catalyst using a solvent selected from the group consisting of methanol-tetrahydrofuran, methanol-dioxane, ethanol-tetrahydrofuran and propanol-tetrahydrofuran.

8. The process according to claim 7, wherein said deacylated compound is reacted with said catalyst at a temperature of from about 0° to about 50° C. and a reaction time of from about 30 minutes to about 24 hours.

9. A process for the production of a ganglioside-related compound which comprises acetylating a compound of the formula

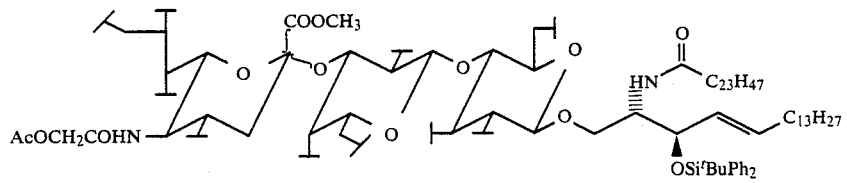

wherein r is OCOCH₃, Ac is COCH₃ and Si$^t$BuPh₂ is a diphenyl-t-butylsilyl moiety to obtain a compound of the formula

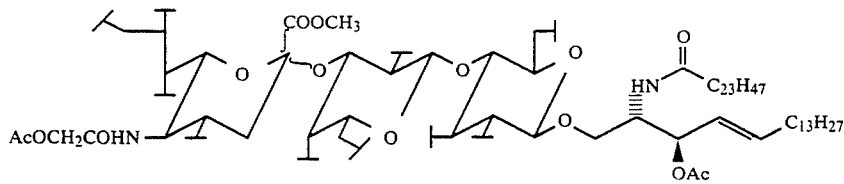

and hydrolyzing said compound to produce a compound of the formula

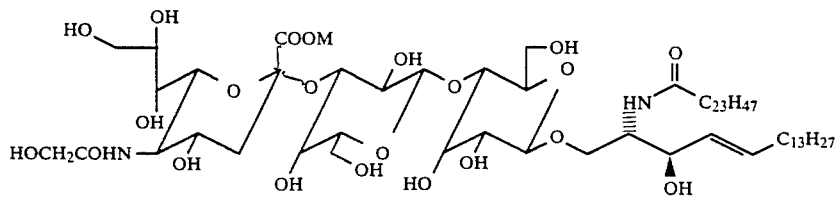

wherein M is an alkali metal ion.

10. The process according to claim 9, wherein the acetylating is carried out by first deprotecting the Si^t-BuPh2 group using a catalyst selected from the group consisting of (C4H9)4NF and HF, followed by acetylation with acetic anhydride or CH3COCl.

11. The process according to claim 10, wherein the deprotecting is carried out in a solvent selected from the group consisting of tetrahydrofuran, CH3CN, CH3NO2, ethyl acetate, CH2Cl2, CHCl3, dimethylformamide, ether, benzene and toluene.

12. The process according to claim 11, wherein the deprotecting is carried out at a temperature of from about 0° to about 50° C. and a reaction time of from about 30 minutes to 48 hours.

13. The process according to claim 10, wherein the acetylation with acetic acid anhydride or CH3COCl is carried out using a solvent selected from the group consisting of pyridine, triethanolamine and dimethylaminopyridine.

14. The process according to claim 13, wherein the acetylation with acetic acid anhydride or CH3COCl is carried out at a temperature of from about 0° C. to about 80° C. and a reaction time of from about 30 minutes to about 24 hours.

15. The process according to claim 9, wherein said hydrolyzing is carried out by first deacetylating said compound

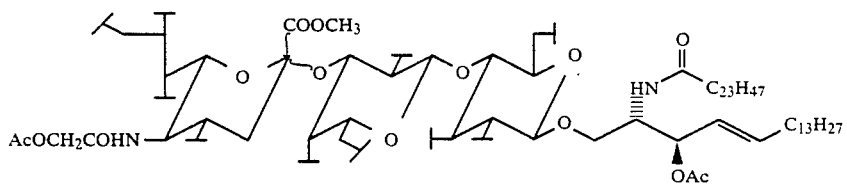

wherein is OCOCH3 and Ac is COCH3 using a catalyst selected from the group consisting of sodium hydride-methanol, potassium carbonate-methanol, potassium hydroxide-methanol and sodium hydroxide-methanol, and then reacting the deacylated compound thus obtained with a catalyst selected from the group consisting of NaOH, KOH and LiOH.

16. The process according to claim 15, wherein said deacylation is carried out in a solvent selected from the group consisting of methanol, ethanol, propanol and tetrahydrofuran and dioxane.

17. The process according to claim 16, wherein said deacylation is carried out at a reaction temperature of from about −10° C. to about 50° C. and a reaction time of from about 30 minutes to 24 hours.

18. The process according to claim 15, wherein said deacylated compound is reacted with said NaOH, KOH or LiOH catalyst using a solvent selected from the group consisting of methanol-tetrahydrofuran, methanol-dioxane, ethanol-tetrahydrofuran and propanol-tetrahydrofuran.

19. The process according to claim 18, wherein said deacylated compound is reacted with said catalyst at a temperature of from about 0° to about 50° C. and a reaction time of from about 30 minutes to about 24 hours.

* * * * *